United States Patent
Owens et al.

(10) Patent No.: US 10,830,750 B2
(45) Date of Patent: Nov. 10, 2020

(54) FUNCTIONAL SOIL MAPS

(71) Applicant: Purdue Research Foundation, West Lafayette, IN (US)

(72) Inventors: Phillip Ray Owens, West Lafayette, IN (US); Hans Edwin Winzeler, Gettysburg, PA (US); Zamir Libohova, West Lafayette, IN (US); Jenette Ashetkar, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 516 days.

(21) Appl. No.: 14/718,856

(22) Filed: May 21, 2015

(65) Prior Publication Data

US 2016/0003792 A1    Jan. 7, 2016

Related U.S. Application Data

(60) Provisional application No. 62/001,114, filed on May 21, 2014.

(51) Int. Cl.
  *G01N 33/24* (2006.01)
  *G06Q 50/02* (2012.01)

(52) U.S. Cl.
  CPC ............. *G01N 33/24* (2013.01); *G06Q 50/02* (2013.01)

(58) Field of Classification Search
  None
  See application file for complete search history.

(56) References Cited

PUBLICATIONS

Zhu et al., "SoLIM: A New Technology for Soil Mapping Using GIS, Expert Knowledge & Fuzzy Logic Overview Prepared by" available at http://solim.geography.wisc.edu/pubs/Overview2007-02-16.pdf as early as in 2010.*
Smith et al., "The effects of DEM resolution and neighborhood size on digital soil survey" Geoderma 137 (2006) 58-69.*
Qi et al., "Knowledge discovery from soil maps using inductive learning" Int. J. Geographical Information Science, 2003, vol. 17, No. 8, 771-795.*
MacMillan et al., "A generic procedure for automatically segmenting landforms into landform elements using DEMs, heuristic rules and fuzzy logic" Fuzzy Sets and Systems 113 (2000) 81-109.*

* cited by examiner

*Primary Examiner* — John C Kuan
(74) *Attorney, Agent, or Firm* — Purdue Research Foundation

(57) ABSTRACT

Embodiments of the present disclosure relate generally to system and methods for generating functional soil maps. The systems and methods are configured to determine soil information for an area of interest; determine an elevation model for the area of interest; determine terrain attributes for the area of interest based on the elevation model; determine a relationship between the soil information and the terrain attributes for the area of interest; and generate a functional soil map based at least in part on the relationship between the soil information and the terrain attributes for the area of interest. In an embodiment, the systems and methods can be used to improve management strategies for crops and other land management regions.

8 Claims, 18 Drawing Sheets

| Functional Classes | Soil Series | Landform | Terrain Attributes | | | | |
|---|---|---|---|---|---|---|---|
| | | | Slope (%) | MRRTF | MRVBF | AACH | TWI |
| 1 | Tilsit, Bedford, Apalona, Johnsburg | Flat Summit | 0 - 2 | > 2.4 | < 2.9 | | |
| 2 | Tilsit, Bedford, Apalona | Summit_Shoulder | 2-6 | > 2.4 | < 2.9 | | |
| 3 | Zanesville, Apalona, Wellston | Summit/Shoulder/Backslope | 6-12 | > 2.4 | < 2.9 | | |
| 4 | Gilpin, Wellston, Adyeville, Ebal | Summit/Shoulder/Backslope | 12-18 | < 2.4 | < 2.9 | | |
| 5 | Gilpin, Ebal, Berks | Backslope/Toeslope/Transitions | 18 - 50 | < 2.4 | < 2.9 | 0.5-2.0 | |
| 6 | Pekin, Bartle | Footslope | 2-12 | < 2.4 | > 2.0 | 0.5-2.0 | |
| 7 | Cuba | Toeslope | 0 - 2 | < 2.4 | > 2.9 | > 0.09 | < 12 |
| 8 | Steff, Stendal, Burnside, Wakeland | Toeslope | 0 - 2 | < 2.4 | 0-1 | < 0.09 | > 12 |
| 9 | | Rock Outcrops, Steep Slope | > 50 | < 2.4 | | | |

*FIG. 9* awc_50.img
<VALUE>
- 0.059999999
- 0.059999999 - 0.109999997
- 0.109999997 - 0.119999997
- 0.119999997 - 0.140588231
- 0.140588231 - 0.160588231
- 0.160588231 - 0.17058823
- 0.17058823 - 0.18058823
- 0.18058823 - 0.190588229
- 0.190588229 - 0.209999993 awc_50_reclass
- 1
- 2
- 3
- 4
- 5
- 6
- 7
- 8
- 9

*FIG. 11* aws_50cm
<VALUE>
■ 3.140000105 - 4.325882411
■ 4.325882412 - 5.511764718
■ 5.511764719 - 6.430823506
■ 6.430823507 - 7.14235289
■ 7.142352891 - 8.239294023
■ 8.239294024 - 8.772941061
☐ 8.772941062 - 9.010117522
☐ 9.010117523 - 9.514117503
☐ 9.514117504 - 10.69999981 aws_50_reclass
■ 1
■ 2
■ 3
■ 4
☐ 5
■ 6
☐ 7
■ 8
■ 9

*FIG. 12*

| Class | PDP | NASIS | Estimated in/hr | Class Code |
|---|---|---|---|---|
| Impermeable | IM | IM | <0.0015 | 1 |
| Very Slow | VS | VS | 0.0015 to < 0.06 | 2 |
| Slow | S | SL | 0.06 to < 0.2 | 3 |
| Moderately Slow | MS | MS | 0.2 to < 0.6 | 4 |
| Moderate | M | MO | 0.6 to < 2.0 | 5 |
| Moderately Rapid | MR | MR | 2.0 to < 6.0 | 4 |
| Rapid | RA | RA | 6.0 to < 20 | 3 |
| Very Rapid | VR | VR | ≥ 20 | 2 |

Note: To convert ìμm / sec (NASIS Permeability, Ksat units) to in / hr, multiply ìm / sec by 0.1417; e.g. (100 ìm / sec) x (0.1417) = 14.17 in / hr. To convert in / hr to ìm / sec multiply by 7.0572

*FIG. 13* ksat_50cm_inches_units
<VALUE>
- ▇ 0.029756999 - 0.06
- ▇ 0.06 - 0.2
- ▓ 0.2 - 0.6
- ▓ 0.6 - 2
- ▒ 2.000000001 - 6
- ☐ 6.000000001 - 20 ksat_50_reclass
- ▓ 1
- ▓ 3
- ▓ 4
- ▓ 5

*FIG. 14*

| VALUE | COUNT | SURFTEXT |
|---|---|---|
| 1 | 8014407 | clay |
| 2 | 2535102 | loamy sand |
| 3 | 3446763 | silty clay |
| 4 | 19013 | sandy loam |
| 5 | 52107 | fine sandy loam |
| 6 | 1087626 | very fine sandy loam |
| 7 | 3522205 | silty clay loam |
| 8 | 3236885 | silt loam |
| 9 | 53158 | loam |

*FIG. 15*

| Drainage Class | PDP CODE | CONV. CODE | Class Code |
|---|---|---|---|
| Very Poorly Drained | IM | IM | 1 |
| Poorly Drained | VS | VS | 2 |
| Somewhat Poorly Drained | S | SL | 3 |
| Moderately Well Drained | MS | MS | 4 |
| Well Drained | M | MO | 5 |
| Somewhat Exc. Drained | RA | RA | 3 |
| Excessively Drained | VR | VR | 2 |

Class code is entered for raster classification purposes. The well-drained soils receive the highest rating and the soils above and below the well-drained receive progressively smaller ratings.

*FIG. 16*

| Functional | | Landform | Soil Depth | | |
| --- | --- | --- | --- | --- | --- |
| Classes | Soil Series | | Soil Survey | OSD | SSURGO-RV |
| 1 | Tilsit, Bedford, Apalona, Johnsburg | Flat Summit | 178 | 198 | 201 |
| 2 | Tilsit, Bedford, Apalona | Summit_Shoulder | 188 | 188 | 201 |
| 3 | Zanesville, Apalona, Wellston | Summit/Shoulder/Backslope | 155 | 165 | 173 |
| 4 | Gilpin, Wellston, Adyeville, Ebal | Summit/Shoulder/Backslope | 134 | 102 | 92 |
| 5 | Gilpin, Ebal, Berks | Backslope/Toeslope/Transitions | 109 | 105 | 69 |
| 6 | Pekin, Bartle | Footslope | 119 | 126 | 201 |
| 7 | Cuba | Toeslope | 119 | 119 | 201 |
| 8 | Steff, Stendal, Burnside, Wakeland | Toeslope | 200 | 200 | 201 |
| 9 | | Rock Outcrops, Steep Slope | 20 | 20 | 20 |

*FIG. 17*

FUNCTIONAL SOIL MAPS

RELATED APPLICATIONS

The present application claims the benefit of U.S. provisional application Ser. No. 62/001,114, filed May 21, 2014, the contents of which are hereby incorporated by reference in its entirety.

STATEMENT OF GOVERNMENT INTEREST

This invention was made with government support under 68-7482-9-543; 2011-68002-30190 awarded by United States Department of Agriculture. The government has certain rights in the invention.

BACKGROUND

Currently, land management decisions are made based on limited data. For example, soil maps are publicly available but the soil maps are usually large scale and provide high level information on the types of soils that may be present in a general area. Even when the high level maps are pixelated, the information stored in the maps does not provide guidance in altering management strategies, e.g., irrigating, pesticide application, etc. Instead, the high level maps provide information on the names and classes of soils present in the area but no information on the functional characteristics of the soils.

Still further, the high level maps do not take into account the topography and landscape effects on the soil characteristics. Topography may interact with soil type to change the preferred or recommended management strategy for a specific area, but the high level maps do not provide information on the interaction between soil type and topography.

Thus, there is a need for a system and method for generating functional soil maps that consider both soil information and topography in order to improve land management practices.

BRIEF SUMMARY

Embodiments of the present disclosure relate generally to systems and methods of generating functional soil maps. In an embodiment, a functional soil map is a map that describes an area not only by its characteristics, e.g., soil names, but by the functional characteristics of the area. In this embodiment, the functional characteristics are affected by the soil type as well as by the terrain attributes, such as slope, aspect, and the like. The functional soil map may be used to assist users in agriculture to improve management techniques. In some embodiments, the functional soil maps are integrated into management systems to adjust irrigation, pesticide application, and the like based on the functional characteristics of the landscape.

In various aspects, systems, computer program products, and computer-implemented methods are provided for generating functional soil maps. The systems, computer program products, and computer-implemented methods are configured to determine soil information for an area of interest; determine an elevation model for the area of interest; determine terrain attributes for the area of interest based on the elevation model; determine a relationship between the soil information and the terrain attributes for the area of interest; and generate a functional soil map based at least in part on the relationship between the soil information and the terrain attributes for the area of interest. The functional soil maps may be used to improve management of fields and other land use regions.

Other aspects and features, as recited by the claims, will become apparent to those skilled in the art upon review of the following non-limited detailed description in conjunction with the accompanying figures.

BRIEF DESCRIPTION OF THE SEVERAL VIEWS OF THE DRAWINGS

Figure 1:
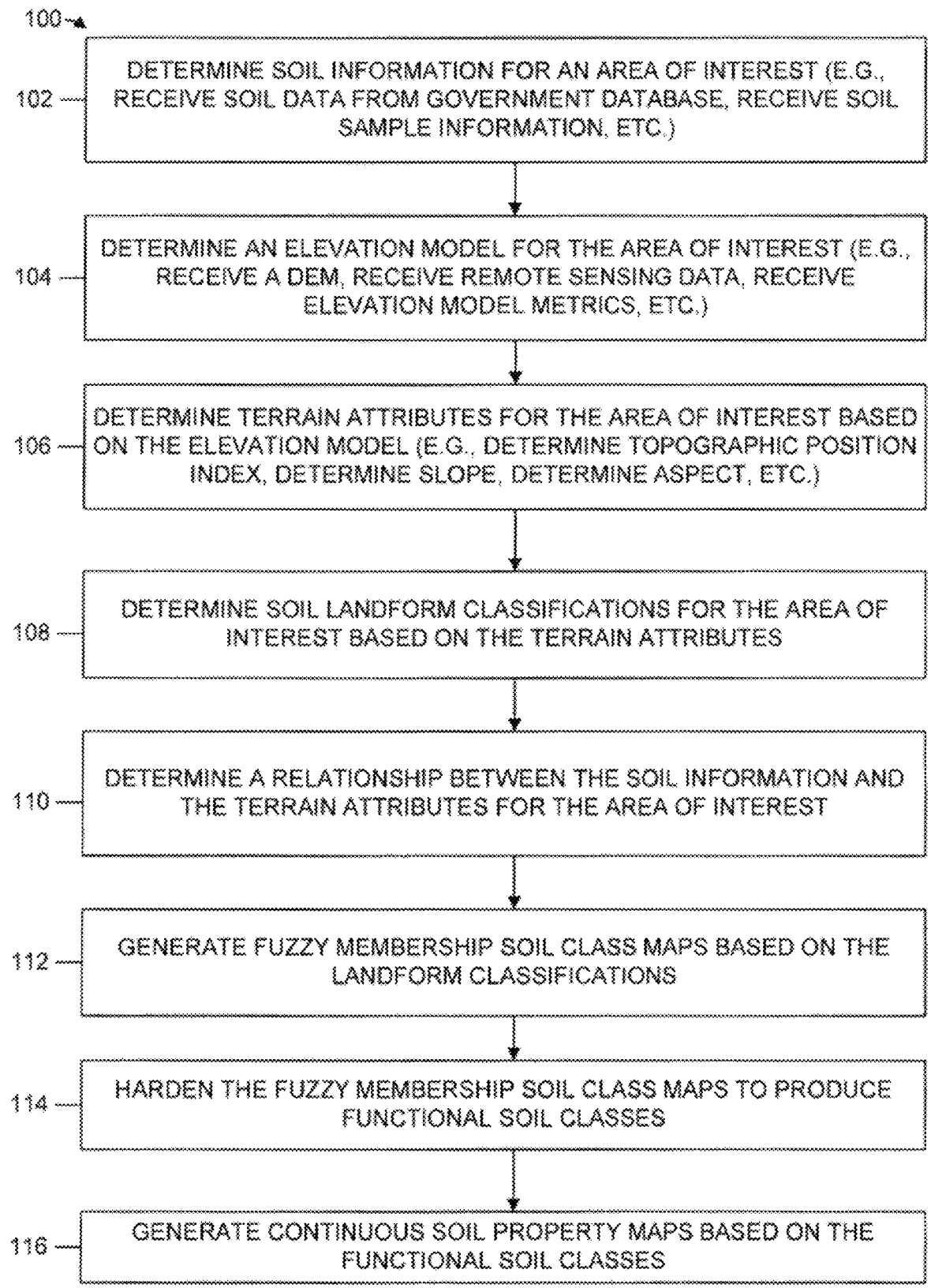
Figure 2A:
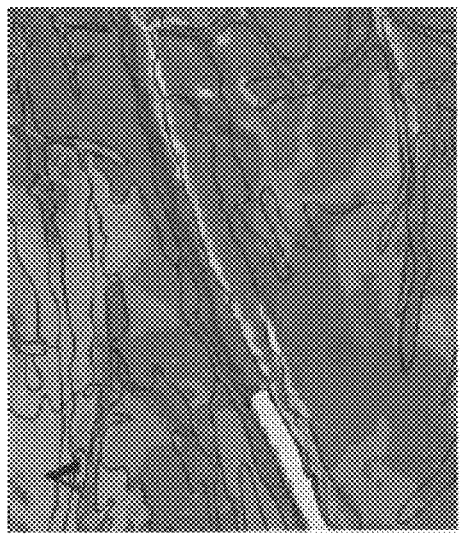
Figure 2B:
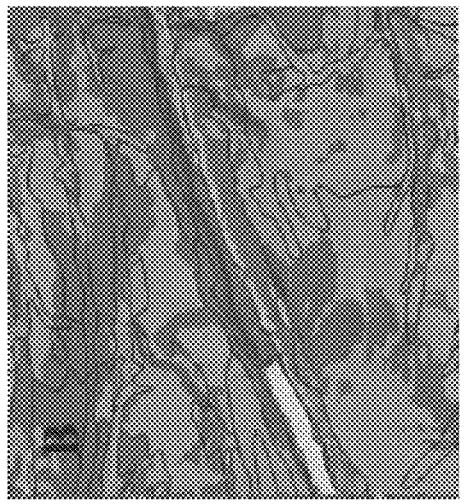
Figure 2C:
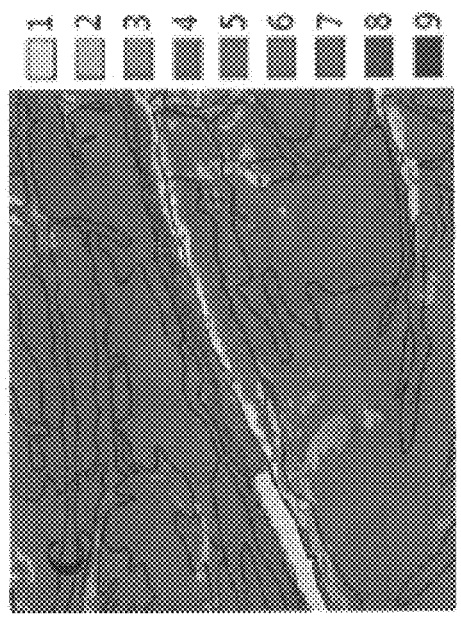
Figure 3:
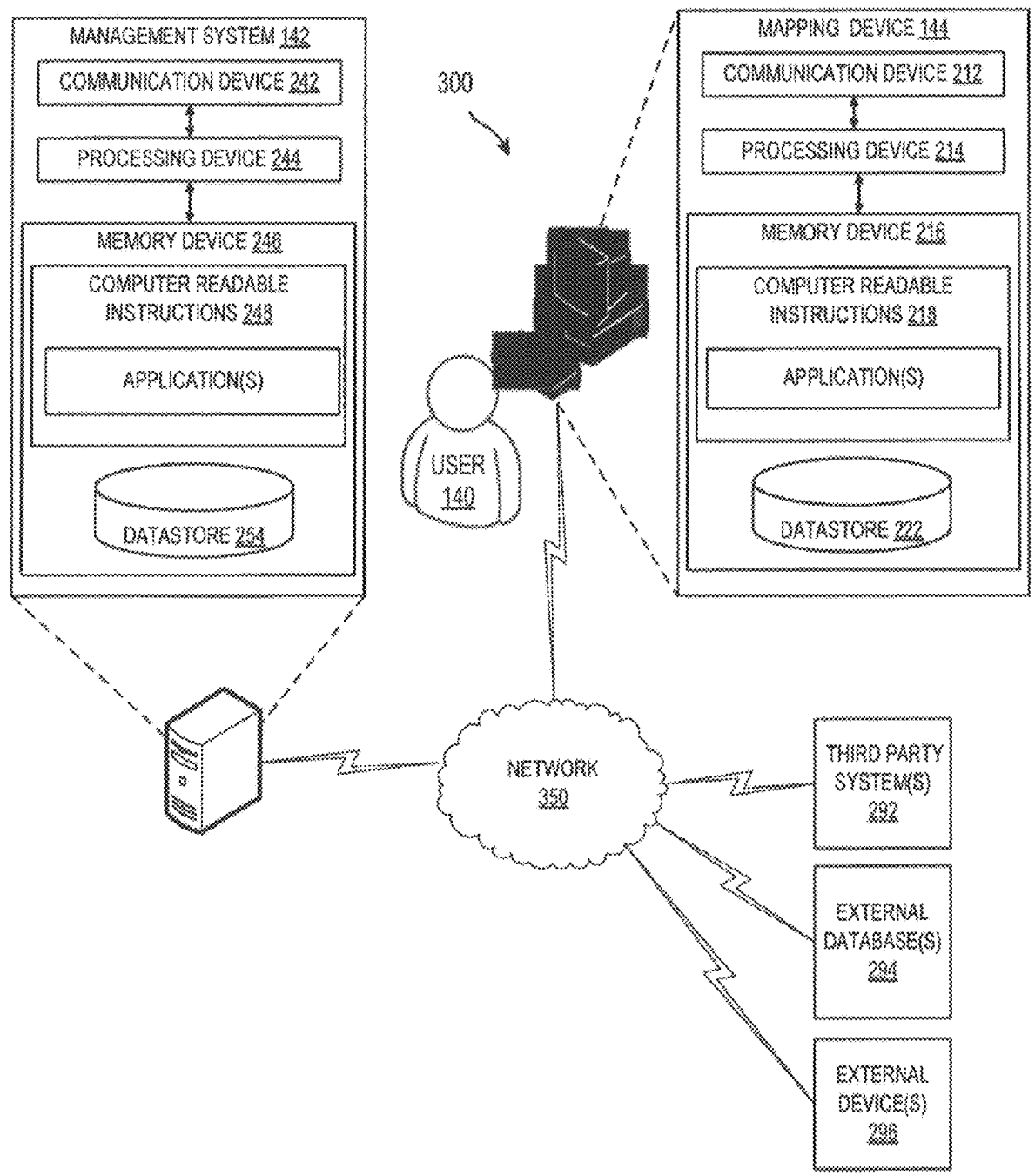
Figure 4:
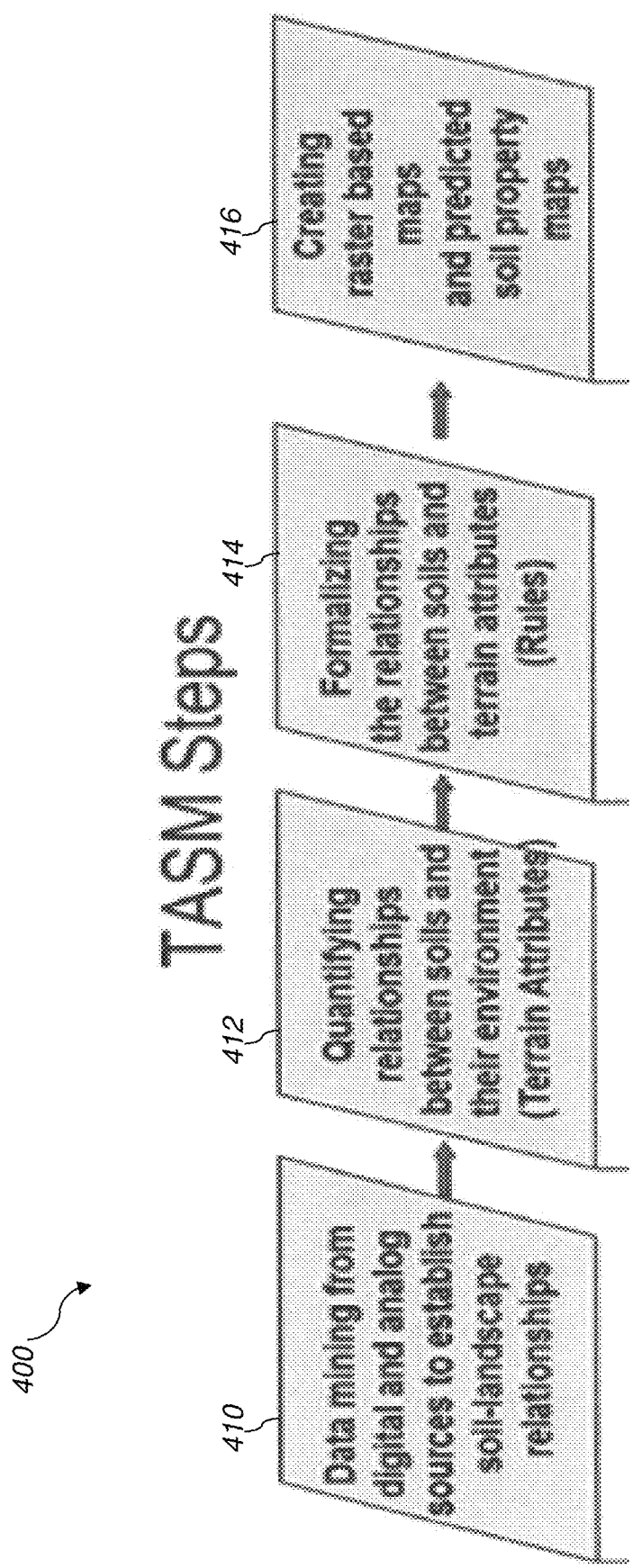
Figure 5:
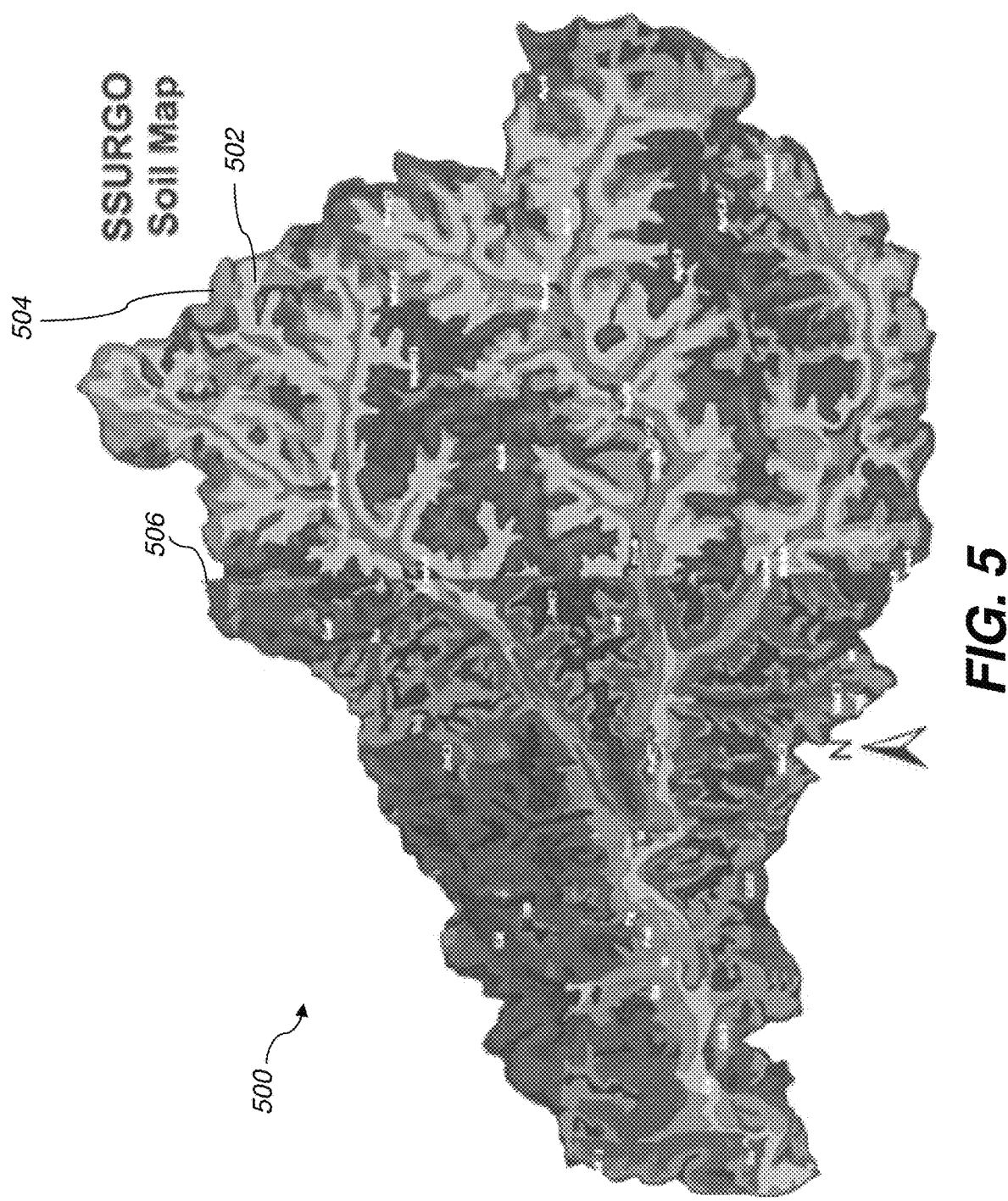
Figure 6:
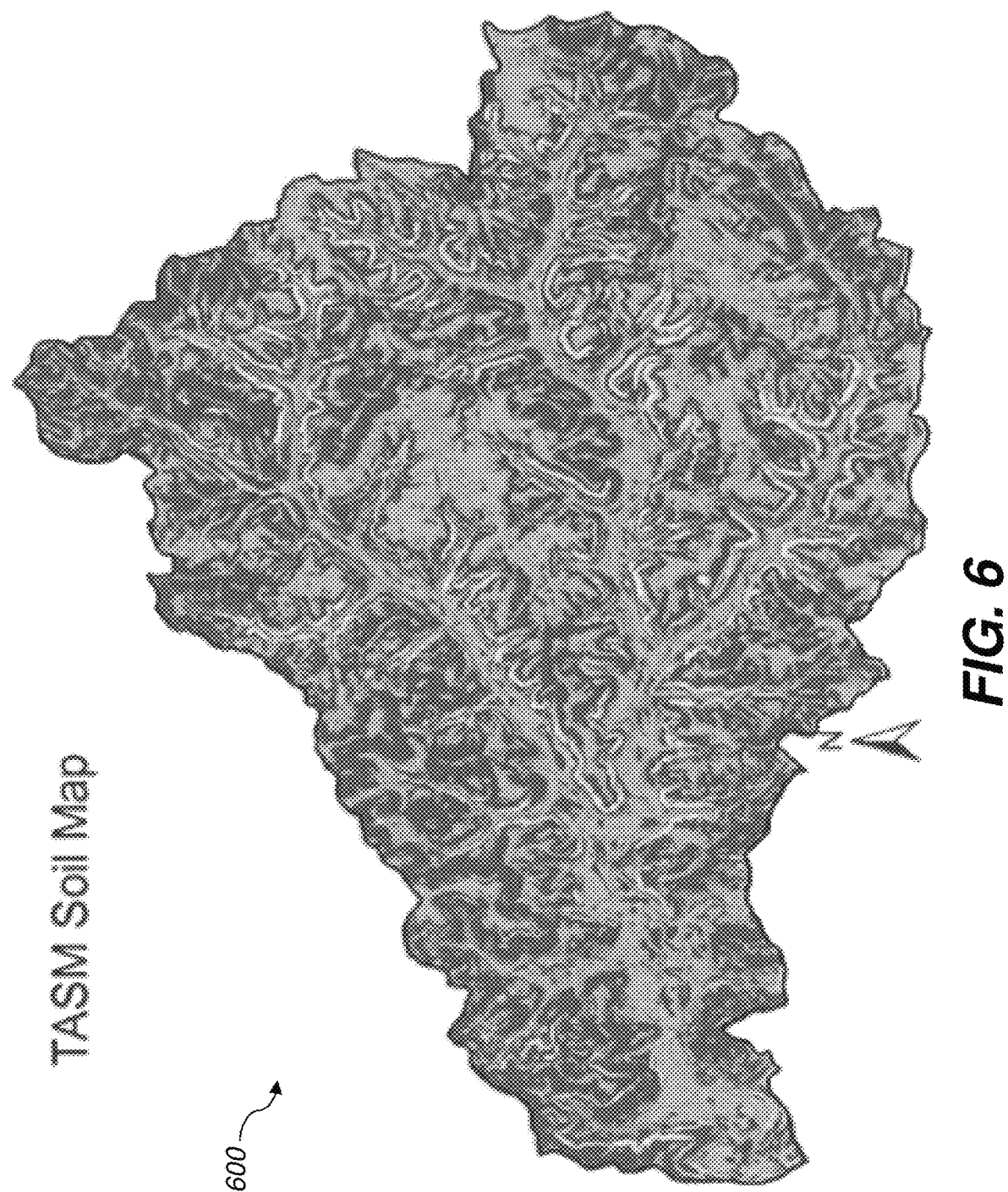
Figure 7A:
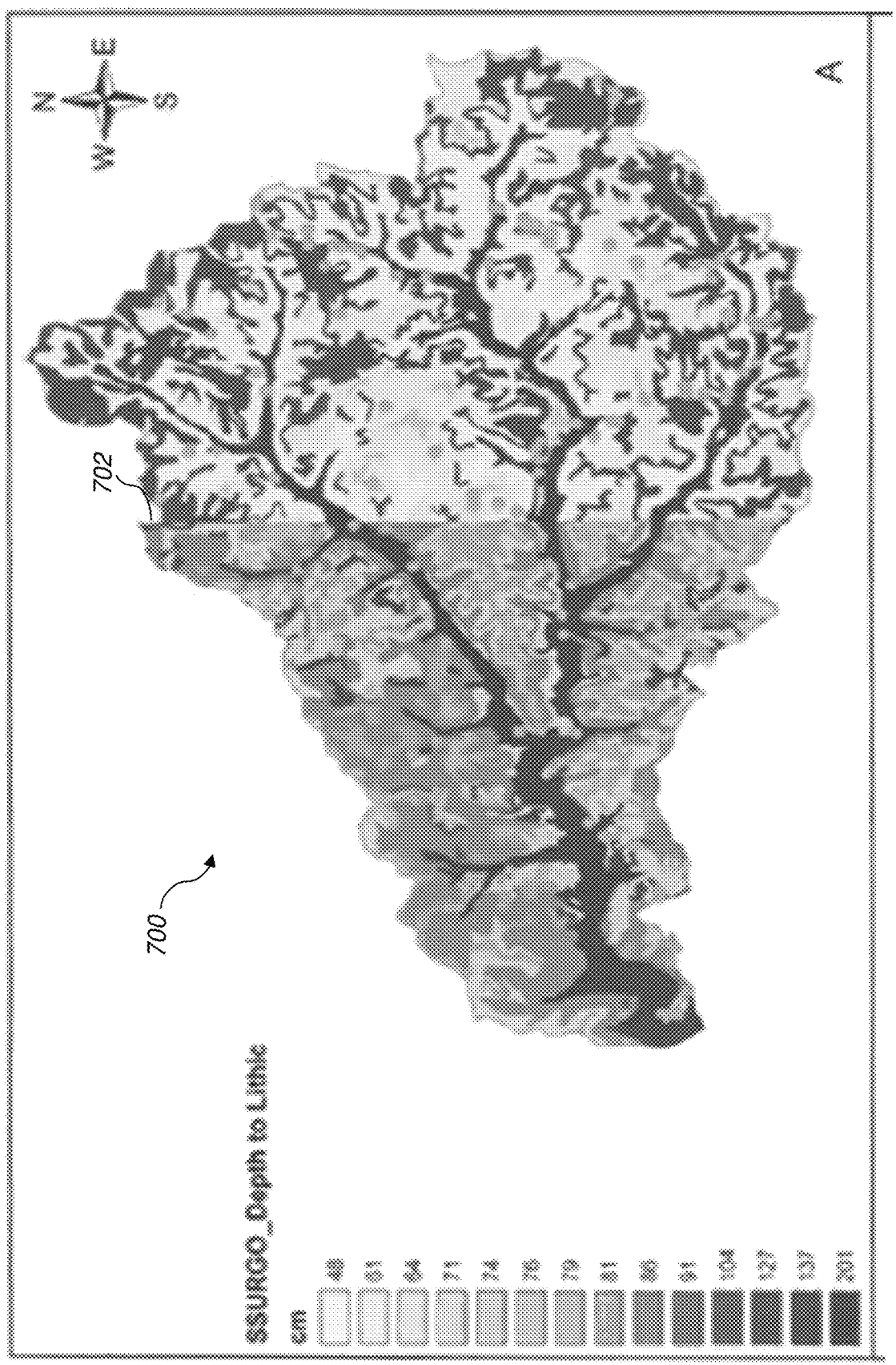
Figure 7B:
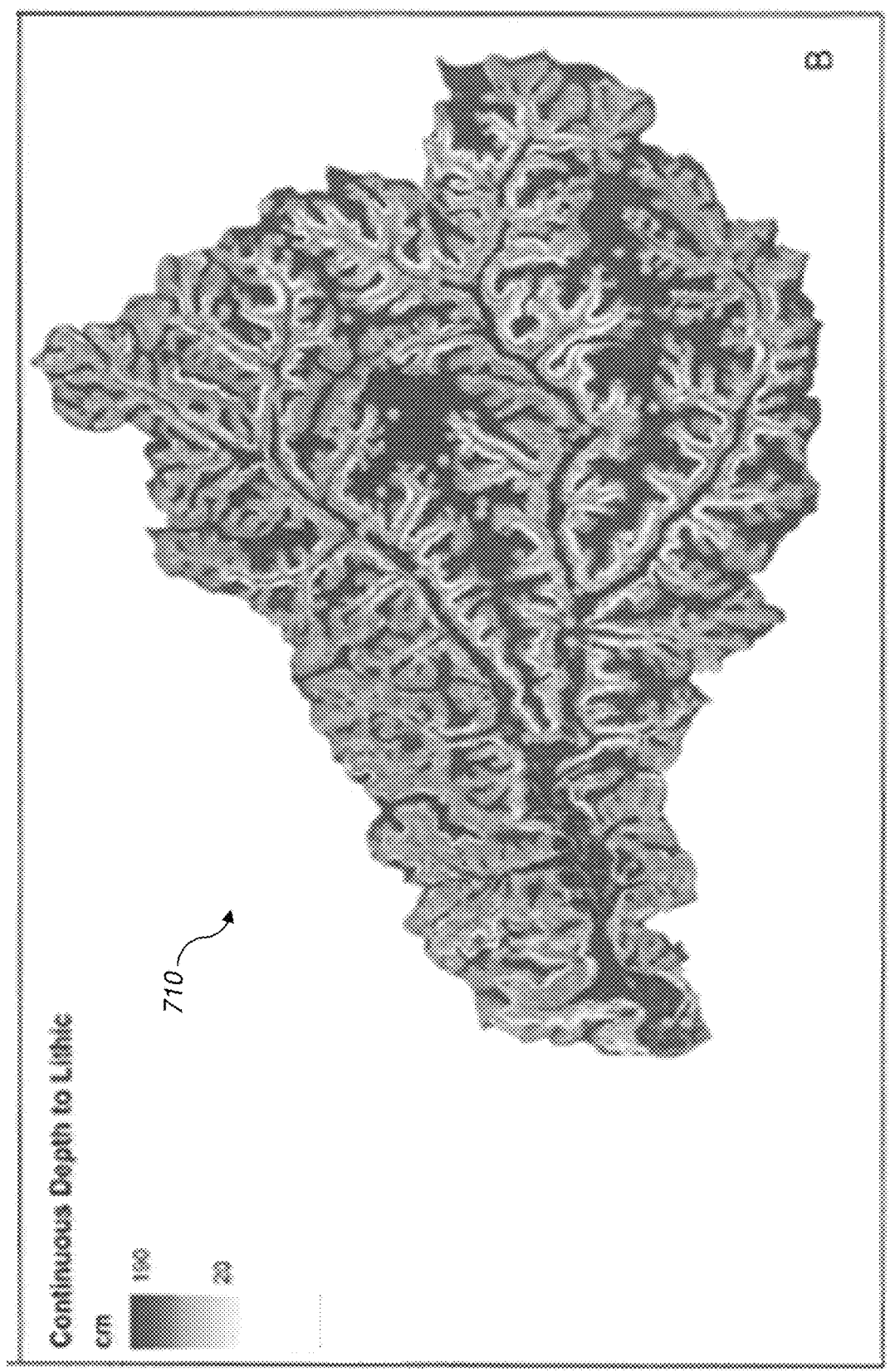
Figure 8:
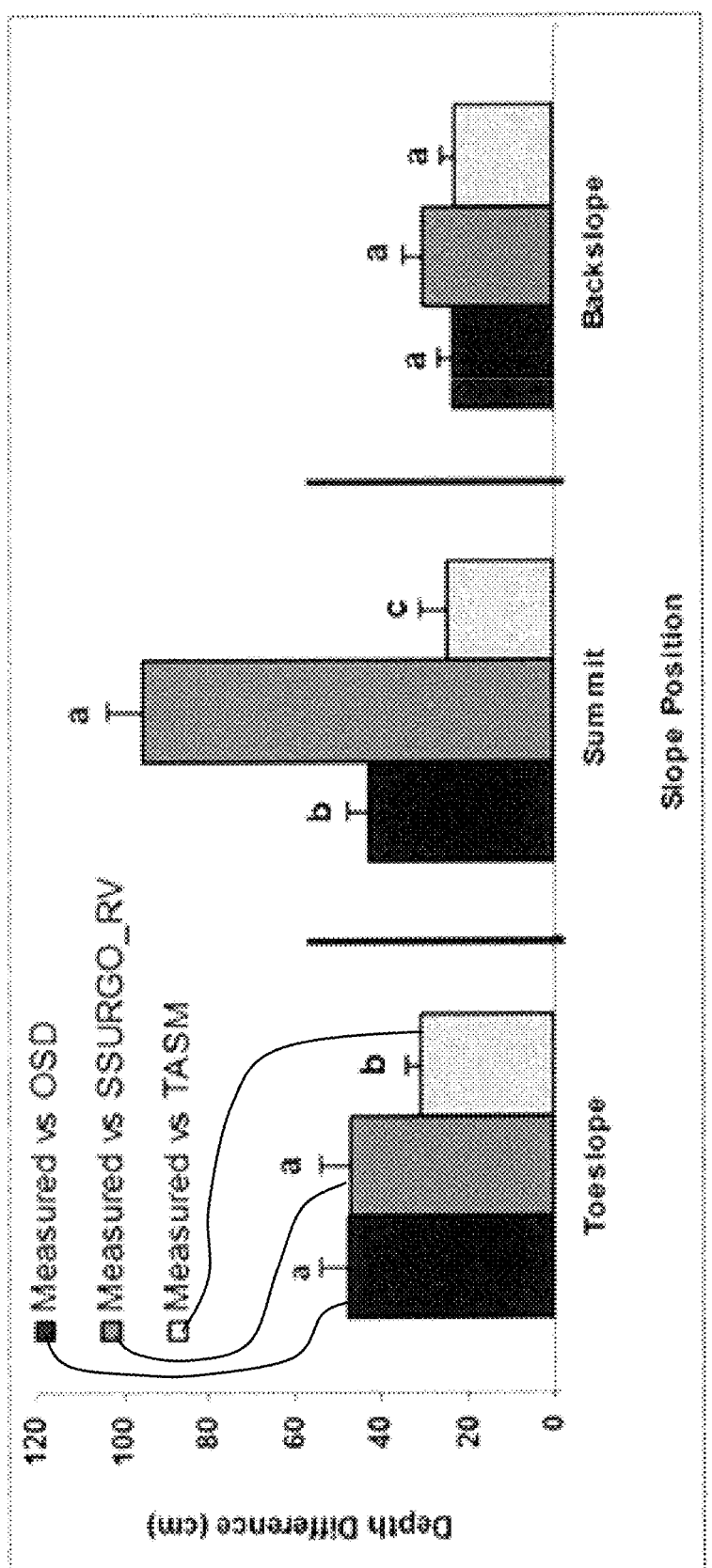

Having thus described embodiments in general terms, reference will now be made to the accompanying drawings, which are not necessarily draw to scale, and wherein:

FIG. 1 provides an exemplary flowchart of a method of generating continuous soil property maps based on functional soil classes, in accordance with one embodiment of this disclosure;

FIGS. 2A, 2B, and 2C provide exemplary raster maps of Potential Soil Productivity Index (PSPI) based on soil characteristics and elevation model derivatives, in accordance with one embodiment of this disclosure;

FIG. 3 provides a block diagram illustrating a functional soil map system, in accordance with an embodiment of this disclosure;

FIG. 4 is a diagram of steps in the Terrain Attribute Soil Mapping process, in accordance with an embodiment of this disclosure;

FIG. 5 is an exemplary SSURGO soil map, in accordance with an embodiment of this disclosure;

FIG. 6 is an exemplary continuous soil map produced via the Terrain Attribute Soil Mapping process, in accordance with an embodiment of this disclosure;

FIGS. 7A and 7B provide a soil depth map generated via SSURGO data (7A) and a continuous soil depth map generated via the Terrain Attribute Soil Mapping process (7B), in accordance with an embodiment of this disclosure; and FIG. 8 provides an exemplary comparison of soil depth differences determined by Official Soil Descriptions, SSURGO data, and the Terrain Attribute Soil Mapping process, in accordance with an embodiment of this disclosure.

FIG. 9 is a table showing functional classes created from numerical relationships between soil series and landforms based on terrain attributes.

Figure 10:
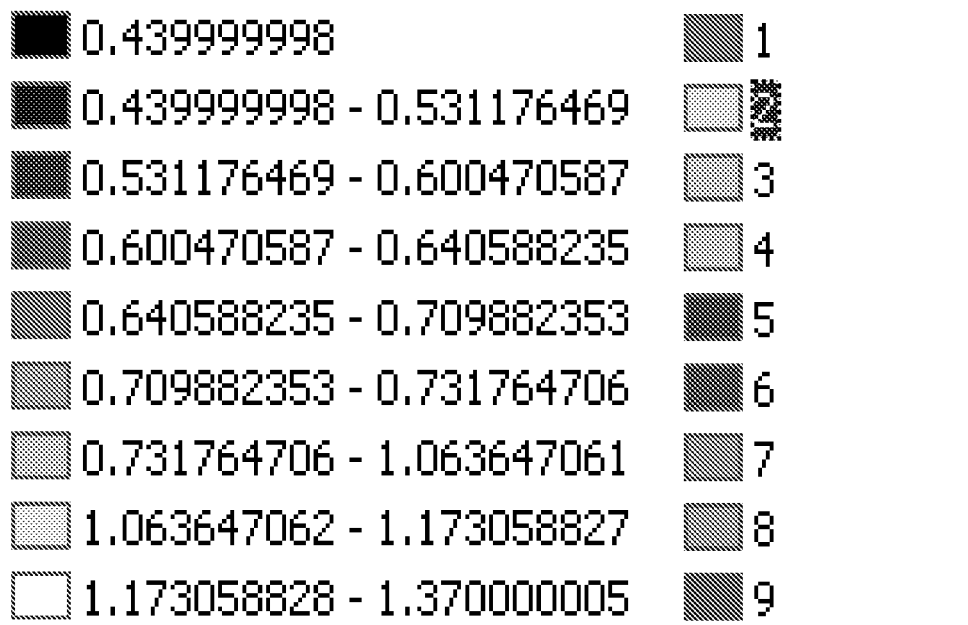

FIG. 10 is a table illustrating an example of how the disclosed system produces a map of organic matter by value up to 50 cm in an area of interest.

FIG. 11 is a table illustrating an example of the AWC soil property, wherein only the representative value is used FIG. 12 is a table illustrating an available water supply example, when a weighted average of all component values is computed and percent composition is the weighting factor.

FIG. 13 is a table showing an example wherein Ksat values are converted to $\mu m*s^{-1}$ to $in*hr^{-1}$: by multiplying with 0.1417 to convert to in/hours.

FIG. 14 is a table showing an example wherein ksat values are rated based on the permeability classes developed by NSSH.

FIG. 15 is a table showing soil surface texture classification.

FIG. 16 is a table showing soil classification based on drainage classes.

FIG. 17 is a table representative soil depth values for different functional classes based on different sources of data.

DETAILED DESCRIPTION

Embodiments of the present disclosure will now be described more fully hereinafter with reference to the accompanying drawings, in which some, but not all, embodiments are shown. Indeed, the disclosure may be embodied in many different forms and should not be construed as limited to the embodiments set forth herein; rather, these embodiments are provided so that this disclosure will satisfy applicable legal requirements. Additionally, while embodiments are disclosed as "comprising" elements, it should be understood that the embodiments may also "consist of" elements or "consist essentially of" elements. Where possible, any terms expressed in the singular form herein are meant to also include the plural form and vice versa unless explicitly stated otherwise. Also, as used herein, the term "a" and/or "an" shall mean "one or more," even though the phrase "one or more" is also used herein. Like numbers refer to like elements throughout.

Throughout this disclosure, various information sources are referred to and/or are specifically incorporated. The information sources include scientific journal articles, patent documents, textbooks, and websites. While the reference to these information sources clearly indicates that they can be used by one of skill in the art, each and every one of the information sources cited herein are specifically incorporated in their entirety, whether or not a specific mention of "incorporation by reference" is noted. The contents and teachings of each and every one of the information sources can be relied on and used to make and use embodiments of the disclosure.

The present disclosure is based on new system and method for analyzing soil information and terrain attributes to create soil maps that provide functional units. These soil maps may be used for agricultural row crop production and as input for hydrological models. This system and method integrates the natural functional properties of soil (soil nutrient content, water content, elevation, altitude, soil structure, soil depth, soil reaction, etc.) and provides the user with information that facilitates decision making for agricultural or preservation purposes. In some embodiments, the system and method are configured to perform the steps of determining soil information for an area of interest, determining an elevation model for the area of interest, determining terrain attributes for the area of interest based on the elevation model, determining a relationship between the soil information and the terrain attributes, determining functional soil classes based on the soil information, landform, and/or terrain attributes, and generating a continuous soil property map based on the functional soil classes.

FIG. 1 provides an exemplary flowchart 100 of a method of generating continuous soil property maps based on functional soil classes, in accordance with an embodiment of the disclosure. In FIG. 1, the blocks describe steps that may be performed by a system, a computer programming product, or a computer-implemented method. In some embodiments, every step in FIG. 1 is not performed in order to generate the continuous soil property maps. Furthermore, additional steps may be performed in addition to the steps disclosed. FIG. 1 is provided as an example of the method and variations on the steps are disclosed herein, all of which are contemplated as included in various embodiments of the system and method.

Turning now to block 102, in some embodiments the system determines soil information for an area of interest. As used herein, soil information includes characteristics and metrics on soil properties of various soil types that are located in the area of interest. For example, soil information may include spatial representations of different soil types in the area of interest. Soil information may also include tabular data of soil properties such as depth of soil, organic carbon, pH, texture, cation exchange capacity, etc. In an embodiment, the soil information is received for use in the system via a computing device processor. In some embodiments, soil information is received or supplemented from multiple databases or sources of information. It should be understood that the soil characteristics disclosed herein are merely exemplary and additional soil characteristics are available.

In some embodiments, the soil information is determined from databases, such as government databases, e.g., the Soil Survey Geographic Database (SSURGO) or the National Cooperative Soil Survey Soil Characterization data. In some embodiments, the soil information is determined from publicly available databases, such as university databases, county offices, or the like. In further embodiments, the soil information is determined from private information, such as business databases, non-profit information, land owner records, or the like. The soil information may be static or dynamic. For example, systems in the area of interest may be configured to dynamically determine soil moisture and update the system with the soil moisture at different intervals. In some embodiments, the soil information is collected by a user, such as via soil samples or via measurement devices that are placed in the field.

In some embodiments, other information is used to supplement the data contained within SSURGO. In an embodiment, SSURGO data is received from a website, such as http://www.nrcs.usda.gov/wps/portal/nrcs/detail/soils/survey/geo/). In further embodiments, the National Cooperative Soil Survey Characterization data is received from a website, such as http://ncsslabdatamart.sc.egov.usda.gov. This database contains measured geo-referenced soil data for many soil properties that are attached to the traditional SSURGO database. In some embodiments, the U.S. Department of Agriculture provides soil data, such as (http://www.nrcs.usda.gov/wps/portal/nrcs/soilsurvey/soils/survey/state/). One of the unique characteristics of the methodology and processes described at this stage is the presence of multiple soil resources that are associated with the area of interest.

In some embodiments, the system determines the soil information from one or more databases. For example, the system may determine an area of interest and identify available soil information from public databases. In some embodiments, the system searches for all available soil information while in other embodiments the system searches for soil information in order of data currency, accuracy, availability, cost, etc. For example, the system may be programmed to first evaluate SSURGO soil data and turn to county-level data if the SSURGO data is not available.

In an embodiment, the soil information is a map comprising one or more polygons corresponding to different soil types. In some embodiments, each polygon includes a primary soil type and one or more secondary soil types that may be present as inclusions in the polygon. In some embodiments, each polygon includes associated data relating to the characteristics of the soil. For example, the polygon may include a reference table that includes soil characteristics such as water holding capacity, cation exchange capacity, and the like, for each soil type. In some embodiments, the soil information is a map comprising a plurality of raster cells, wherein each cell includes information on one or more soil types. For example, a raster cell may have a value for each soil type in the area of interest, e.g., 70% soil A, 20% soil B, and 10% soil C. In some embodiments, a value of the raster cell corresponds to a characteristic of the soil in the cell.

As used herein, an "area of interest" is an area for which a functional soil map is being prepared. For example, the area of interest may be a field, a building site, a nature reserve, or the like. In an exemplary embodiment, the area of interest is a field for crops wherein the field has divergent topography and/or soil types that makes determination of the functional soil map useful for optimizing planting, harvesting, watering, fertilizing, pesticide application, and/or some other crop management strategy.

An area of interest may be determined by receiving geographic coordinates that define edges or borders of the area of interest. For example, a map may be received that includes polygons delineating one or more areas of interest. In another embodiment, coordinates, e.g., GPS coordinates, are used to identify the corners of the area of interest. In some embodiments, an area of interest is defined by another area. For example, a buffer around a water source may be considered an area of interest, or all of the area in a map that is a predetermined distance from roads in the map. There are many ways of identifying an area of interest, as known in the art, and the examples provided in this specification are not intended to be limiting.

In some embodiments, the system calculates the center point locations for the SSURGO map unit polygons using a polygon to feature command. In an embodiment, the point is placed in the geometric center of each polygon. In this embodiment, the system then extracts the soil property information at the center point to determine each soil property of interest. The attribute values in SSURGO are typically identified in ranges but also provide a representative value (RV) commonly referring to the midpoint of the range. The assumption is that the center of a polygon represents the most likely location of the central concept of the mapped soil with the ideal properties. In some embodiments, after locating the centroid or central concept a quantitative geo-statistical technique is applied to provide continuous soil property predictions through interpolation.

As discussed, soil information may come in many different forms and from many different sources. Soil information is often presented as polygons in a map of an area. Unfortunately, the available maps do not provide a functional soil map. Instead, the maps define the soils in terms of soil name and ranges of characteristics. These maps are not useful for assisting users in managing fields or other areas of interest because: (1) the soil information present in the maps is not in a form that correlates to management principles and practices, (2) the map do not take into account the terrain attributes that combine with the soil characteristics to influence management practices, and (3) the current soil maps are polygons with one unique value for the entire polygon, which may cover hundreds of acres. In contrast, the current system provides unique soil estimates at the resolution of the underlying data (e.g., the DEM). These properties can be grouped or provided in raster format. Thus, the system uses soil information but goes beyond the soil information to provide practical and applicable functional soil maps to assist users in management practices.

In block 104, in some embodiments the system determines an elevation model for the area of interest. As used herein, an elevation model is a computer representation of elevation and/or topography in the area of interest. For example, the elevation model may be a digital elevation model (DEM) used in geographic modeling. The elevation model may have a variety of resolutions including sub-meter, 10×10 m, and 30×30×m pixels. In an embodiment, the elevation model is created from remotely sensed data. The 10×10 and 30×30 are available nationwide and are provided for free by the USGS websites, but also by USDA-NRCS at http://datagateway.nrcs.usda.gov/. The resolution of spatial data continues to improve. The USDA is currently investing in collecting finer resolution DEM at sub-meter level also known as Light Detection and Ranging (LiDAR) for the entire nation with priority to agricultural areas. Currently the LiDAR data is available for free at http://datagateway.nrcs.usda.gov/. It is also available for purchase for modest fees from various vendors. Despite the finer resolution of LiDAR, the majority of the soil surveys conducted in the U.S. do not justify the use of sub-meter pixel size.

In some embodiments, the elevation model is a digital elevation model received from an online resource. In an embodiment, the elevation model is a source of information on the landscape and features of the area of interest that may be used with the soil information to provide additional insight into the spatial distribution of soils and their properties. In some embodiments, the system receives an elevation model having a resolution between 5-10 m, which is suitable given the scales of soil surveys and adequate for accurate spatial representation of soils and soil properties. It should be understood that elevation models having higher or lower resolution may also be used, including higher resolution elevation models when higher resolution soil information is available. In some embodiments, a finer resolution elevation model is resampled to coarser resolution to improve the prediction of soil function types. This resampling may be accomplished using ArcMap software or other spatial analysis software.

In some embodiments, the elevation model is preprocessed prior to use with other data types. For example, in some embodiments the elevation data goes through iteration of resampling and filtering/smoothing in order match the scales of soil data with the resolution of DEM and/or LiDAR. This process may assist in establishing the soil landscape-terrain attribute relationships. This procedure allows for the conditioning of the elevation data and is conducted in ArcMap using several modules contained in ArcToolBox. Other preprocessing techniques include fill gaps, fill sinks, and sink removal.

In block 106, in some embodiments the system determines terrain attributes for the area of interest based on the elevation model. In some embodiments, a terrain attribute is a metric related to and calculated at least in part on the elevation model. For example, slope and aspect of a specific part of the area of interest are terrain attributes that may be calculated from an elevation model. The combination of elevation models and soil information relating to soils, soil processes, and their properties allows for the quantification of soil-terrain relationships. In some embodiments, the understanding of soil-landscape relationships is used to spatially associate soils with terrain characteristics.

In some embodiments, terrain attributes are algorithms that are applied to a digital elevation model and provide unique values for each pixel on the surface. Multiple terrain attributes may be used in this process. Some of the terrain attributes include: topographic wetness index (TWI), slope, altitude above channel network, valley bottom flatness, catchment area, elevation, curvature (planform, profile curvature), morphometric features, relative heights and slope position, aspect, terrain ruggedness index, terrain surface convexity, terrain surface texture, topographic position index (TPI), TPI based landform classification, valley and ridge detection, slope length stream power index, geomorphons, Iwahashi and Pike, Hammond, etc. It should be understood that additional terrain attributes may be determined from an elevation model and the examples disclosed herein are not limiting.

In an embodiment, these terrain derivatives and surface classifications are developed through System for Automated Geoscientific Analysis (SAGA) software (http://www.saga-gis.org/en/about/software.html) and/or ArcMAP (http://www.esri.com/software/arcgis) and other available spatial analysis software. The ability of each terrain attribute to highlight various landscape positions suggests the use of many terrain attributes to allow for the accurate and explicit spatial representation of soils and their properties in the landscape. SAGA is free and open source software and one of the most powerful tools used for spatial analysis. The software has a variety of tools and modules that are used for deriving over eighty terrain attributes from DEMs and for conducting quantitative analysis of soil-landscape relationships.

In some embodiments, the system selects and or modifies terrain attributes. For example, the system may identify multiple different landforms based on terrain attributes and aggregate the different landforms based on similar soil function. The current landform algorithms are designed to delineate geomorphic landforms, not to classify soils. These algorithms produce too many landforms and result in inaccurate or overly complex models of soil function. For example, delineating landforms on a 40 acre farm field using the terrain attribute geomorphons would classifies 9 or 10 different landforms, but there are likely only 3 to 4 functionally different soil types occurring in those landforms. Thus, in some embodiments, the system groups landforms together to more accurately represent soil classes and to address the issue of some classes having a relatively small number of pixels. Research has found that some of the geomorphon landforms do not significantly differ with respect to terrain attributes. For example, depressions, hollows, footslopes, and valley landforms classified according to geomorphons are not significantly different from each other with respect to Topographic Wetness Index and can be grouped together. Because the values of terrain attributes are not normally distributed, in some embodiments rank-sum tests are used to determine if the classes are statistically different with respect to terrain attribute (TWT, slope, etc.). The classifications used in the examples were geomorphons and IWPike.

In block 108, in some embodiments the system determines soil landform classifications for the area of interest based on the terrain attributes. Examples of landforms include flat summit, summit shoulder, footslope, toeslope, rock outcrops, etc. Landforms are characteristic areas in the area of interest that are defined by their geography, terrain, and/or soil characteristics. Landforms typically are more likely to share common attributes than different landforms. For example, two areas categorized as flat summits may be more likely to have similar levels of water availability, hours of direct sunlight, depth of soil, and the like, compared to a flat summit and a footslope. In some embodiments, the soil landform classifications are based on their differences in performance under the same management strategy instead of based on the soil series level. For example, some soil landforms may differ in performance when under no-till management.

In block 110, in some embodiments the system determines a relationship between the soil information and the terrain attributes for the area of interest. In some embodiments, once the terrain attributes are developed the next step is the establishment of relationships between terrain attributes and soils. This step involves a numerical analysis of terrain attribute spatial characteristics that enhances the knowledge about spatial soil setting in the area of interest. The use of various sources such as published soil polygon maps like SSURGO, tabular data, soil map unit descriptions from published soil survey manuals, and published official soil series descriptions allows for the establishment of conceptual soil landscape-terrain attribute relationships that are described with qualitative statements. In an embodiment, this step is followed by the numerical quantitation of the soil-landscape relationships for the predictions of soil properties based on the unique pixel values from the terrain attributes. The establishment of numerical soil landscape terrain attribute relationships is performed via several means. These may include the Soil Landscape Inference Model (SoLIM) or Arc Soil Inference Engine (ArcSIE) software and the Knowledge Miner, zonal statistics and raster calculations processes in ArcMap and other spatial analysis software, histogram analysis and frequency distribution functions in ArcMap, SAGA and other spatial analysis software.

In an embodiment, these numerical relationships allow for the assignment of soils to various soil landscape positions in a semi-automatic and automatic manner using fuzzy logic (FIG. 9). The fuzzy logic allows for the generation of fuzzy membership soil classes to each pixel that vary from 0 (no membership) to 100 (full membership). This mechanism allows for the generation of continuous soil maps that honor the natural variability of soils in the landscape contrary to the soil polygon maps. This mechanism also provides the base for the generation of continuous soil property maps. ArcSIE (http://www.arcsie.com/index.htm), which is an extension of ArcMap software can also be used for this process. In addition to ArcSIE, the system may use an algorithm that allows for the determination of soil membership using fuzzy logic that results from zonal statistic, raster calculator, histogram analysis, and frequency distribution functions.

In some embodiments, the system develops soil landform classifications based on knowledge of soil formation and soil function. In an embodiment, the system classifies soils based on their differences in performance under the same management strategy. The soil characteristics that are used to determine the raster cell characteristics may be derived from various sources. For example, the government database, e.g., SSURGO, includes information on soil types and corresponding characteristics. In further embodiments, the soil characteristic data may be sampled directly from the area of interest. For example, representative soil types in the area of interest can be identified and soil characteristics determined.

In a further embodiment, the system determines the soil landform classification by using multiple linear regressions to determine the terrain attributes most strongly correlated with the soil information, e.g., SSURGO property representative value, in the polygon representing the soil type. In an embodiment, the soil polygon is converted to a raster layer. The system extracts every pixel in the soil raster layer and all terrain attributes for the corresponding raster maps of the area of interest. The system then uses cluster analysis and, in some embodiments, multiple regressions to identify where soil types and terrain attributes coincide. In some embodiments, the soil type/terrain attributes are evaluated and clusters of soil types correlating with terrain attributes are identified. For example, soil type A raster cells may cluster within a specific range of TWI, slope, and aspect. Soil type B raster cells may cluster within a different range of TWI, slope, and aspect.

In some embodiments, the system identifies the average terrain attributes for the cluster, e.g., average TWI, average slope, and average aspect, and assigns the soil 100% membership at those terrain attributes. For example, soil A may cluster within a range of TWI, aspect, and slope. The system determines that the average TWI is X, the average aspect is Y, and the average slope is Z for soil A cells in the cluster. The system assigns soil A as 100% membership in raster cells that have a TWI of X, an aspect of Y, and a slope of Z. The system then continues this classification process for all soil types in the area of interest.

In some embodiments, once the 100% membership cells in the various soil types are identified based on cluster analysis cells that are not a 100% match to a soil type are classified. For example, a raster cell may have a TWI, aspect, and slope that is 90% similar to soil A and 10% similar to soil B. The cell will be assigned two or more soil types and a value indicating the influence of that soil type on the cell.

In an embodiment, a map is created for each soil type in the area of interest. Each map applies to a single soil type and the value of each cell in the map corresponds to the percentage of that cell that is applied to the single soil type. For example, a first map may be created for soil type A. Each cell in the map ranges from 0% to 100% and provides the value of soil type A in that cell. Another map may be created for soil type B and each raster cell in this map includes a value that is the proportion of the cell assigned to soil type B, e.g., 0% to 100%. In an embodiment, the values of the raster cells add up to 100%. In some embodiments, however, the values do not add up to 100% because of rounding or because of different types of surfaces in the area of interest, e.g., water.

In a still further embodiment, co-kriging and/or regression kriging may be used to determine a relationship between the soil information and the terrain attributes for the area of interest. For example, co-kriging is used in digital soil mapping to interpolate between known data points by incorporating corollary and spatially related information. This corollary information, known as environmental covariates (terrain attributes), refers to features which vary spatially along with the known data points in a predictable and quantifiable manner. These relationships are then used within the model development to improve interpolated results between points. Regression kriging is a hybrid method combining linear regression and ordinary kriging. With regression kriging, the target soil property variable is predicted using the modeled linear regression equation and kriged values. The ordinary kriged map is then added to a kriged map of the residuals to produce a smoother regression interpolated kriged map. The resulting soil property predictions from the co-kriged map or the regression kriged map is a product that provides continuous soil property predictions and can be combined for a soil productivity index. In some embodiments, the centroid of a polygon is determined and a map is created via kriging between known points on the map, e.g., between centroids of different polygons. The kriging method may be further influenced by topography such as the elevation model or derivative thereof. In some embodiments, a data point is generated at the geometric center of a polygon based on the USDA maps. The system then utilizes geostatistics to provide a continuous surface.

In further embodiments, the system determines a relationship between the soil information and the terrain attributes for the area of interest by determining continuous soil functional maps. For example, the system may determine a potential soil productivity index (PSPI) for the area of interest or subsets of the area of interest. In an embodiment, the system combines soil information, e.g., SSURGO polygon soil property data, with terrain attributes, such as Topographic Wetness Index (TWI), to create continuous maps of Potential Soil Productivity Index (PSPI) as one of the many applications that can be developed from the data. This methodology takes into account the water redistribution in the landscape that is represented by TWI and combines it with other water related soil properties (e.g., Organic Matter—OM, surface soil texture—ST, Available Water Capacity—AWC, Available Water Supply—AWS, soil saturated hydraulic conductivity—Ksat) to create continuous PSPI maps. These maps provide guidance for the farmers at farm level to address uncertainties in climate fluctuations, especially precipitation amount and distribution, by representing potential soil behavior in a spatially explicit way allowing a targeted management of crops and water.

In some embodiments, software such as ArcMap's Soil-Data Viewer extension, may be used to develop the ratings. In some embodiments, the rating is developed based on soil properties such as Organic Matter (OM), available water capacity (AWC), available water supply (AWS), Ksat, and Surface Texture (ST). In an exemplary embodiment, the rating is from 1-9 with 1 being the worst and 9 being the best condition. For the OM, AWC, and AWS higher values receive higher rating. However, the rating for the Ksat and surface texture are based on their influence on the ability of plants to use the water without spending too much energy. Clay and sandy soils receive lowest ratings and highly permeable and restrictive Ksat receive lower ratings. The OM, AWC, AWS, and Ksat are calculated for the 0-50 cm depths assuming that the majority of the plant roots extend through this layer. Texture is only for the surface layer and can be modified if needed. Examples of ratings for soil characteristics for OM, AWC, AWS, Ksat, ST, and drainage class are provided in order to provide guidance in one embodiment of this disclosure and are not intended to limit the disclosure to only using these characteristics or to be bound to using these characteristics. Other characteristics, in addition to or instead of the example disclosed herein, may be used to rate soils for functional soil maps.

As used herein, "Organic Matter" (OM)" is the plant and animal residue in the soil at various stages of decomposition. In an embodiment, the organic matter value is converted into or provided as organic carbon using well-established conversion factors. The estimated content of organic matter is expressed as a percentage, by weight, of the soil material that is less than 2 millimeters in diameter. SoilDataViewer should be in Advance Mode in order to see all the estimated values for the properties to be used for the rating. For example, the aggregation method may be weighted average and the depth range may be 50 cm. The polygons may be converted to raster and the system may use the cell size that is equivalent to the elevation model cell size or its derivative TWI. In an embodiment, the OM raster map may be snapped, or fitted, to the TWI map. The number of classes may be determined, for example 9 classes, although more or fewer classes may be defined depending on the needs of the user and the variation in the underlying data layers. In some embodiments, the classification is according to natural breaks, i.e., jenks, and the field is the value. Other classifications may also be used, including equal breaks (e.g., quintiles for five classifications), defined breaks (e.g., user-defined classes), or the like. FIG. 10 illustrates an example of how the system produces a map of organic matter by value up to 50 cm in an area of interest.

As used herein, "available water capacity" (AWC) refers to the quantity of water that the soil is capable of storing for use by plants. The capacity for water storage is given in centimeters of water per centimeter of soil for each soil layer. The capacity varies, depending on soil properties that affect retention of water. The most important properties are the content of organic matter, soil texture, bulk density, and soil structure. In some embodiments, corrections for salinity and rock fragments are made. Available water capacity is an important factor in the choice of plants or crops to be grown and in the design and management of irrigation systems. It is not an estimate of the quantity of water actually available to plants at any given time.

For each soil layer, AWC is recorded as three separate values in the database. A low value and a high value indicate the range of this attribute for the soil component. A "representative" value indicates the expected value of this attribute for the component. For this example of the AWC soil property, only the representative value is used, as illustrated in FIG. 11.

As used herein, "available water supply" (AWS) is the total volume of water that should be available to plants when the soil, inclusive of rock fragments, is at field capacity. It is commonly estimated as the amount of water held between field capacity and the wilting point. In some embodiments, corrections for salinity, rock fragments, and rooting depth are made. AWS is reported as a single value of water for the specified depth of the soil. AWS is calculated as the available water capacity times the thickness of each soil horizon to a specified depth. In an embodiment, the available water supply for each map unit is aggregated to a single value for the map unit by the process described below. For example, if AWC is 0.15 cm/cm, the available water supply for 25 centimeters of soil would be 0.15×25, or 3.75 centimeters of water.

A map unit typically consists of one or more "components." A component is either some type of soil or some non-soil entity, e.g., rock outcrop. For the attribute being aggregated (e.g., available water supply), the first step of the aggregation process is to derive one attribute value for each of a map unit's components. From this set of component attributes, the next step of the process is to derive a single value that represents the map unit as a whole. Once a single value for each map unit is derived, a thematic map for the map units can be generated. Aggregation is needed because map units rather than components are delineated on the soil maps. The composition of each component in a map unit is recorded as a percentage. For example, a composition of 60 indicates that the component typically makes up approximately 60 percent of the map unit. For the available water supply example, when a weighted average of all component values is computed, percent composition is the weighting factor, as illustrated in FIG. 12.

Saturated hydraulic conductivity (Ksat) refers to the ease with which pores in a saturated soil transmit water. In an embodiment, the estimates are expressed in terms of micrometers per second. The estimates are based on soil characteristics observed in the field, particularly structure, porosity, and texture. Saturated hydraulic conductivity is considered in the design of soil drainage systems and septic tank absorption fields. In an embodiment, for each soil layer this attribute is recorded as three separate values in the database. A low value and a high value indicate the range of this attribute for the soil component. A "representative" value indicates the expected value of this attribute for the component. For this soil property, in some embodiments only the representative value is used. For example, the numeric Ksat values may be grouped according to standard Ksat class limits. In this example, the values are converted to $\mu m*s^{-1}$ to $in*hr^{-1}$: by multiplying with 0.1417 to convert it to in/hours, as shown in FIG. 13. In an embodiment, the permeability code criteria are derived from Schoeneberger, P. J., Wysocki, D. A., Benham, E. C., and Broderson, W. D. (editors), 2002. *Field book for describing and sampling soils*, Version 2.0. Natural Resources Conservation Service, National Soil Survey Center, Lincoln, Nebr., which is hereby incorporated by reference.

In some embodiments, the ksat values are then rated based on the permeability classes developed by NSSH (Soil Survey Staff, 2001). If a class is not present in the area of interest, then the class is not rated based on permeability classes. In this example, class 2 was not present in the area of interest and therefore is not rated, as shown in FIG. 14.

As used herein, "surface texture" (ST) refers to the representative texture class and modifier of the surface horizon for the soil. The dominant condition specified for the soil type was used as shown in FIG. 15. Texture is given in the standard terms used by the U.S. Department of Agriculture. These terms are defined according to percentages of sand, silt, and clay in the fraction of the soil that is less than 2 millimeters in diameter. "Loam," for example, is soil that is 7 to 27 percent clay, 28 to 50 percent silt, and less than 52 percent sand. In some embodiments, if the content of particles coarser than sand is 15 percent or more, an appropriate modifier is added, for example, "gravelly."

In an embodiment, clay is rated as 1 due to the fact that in most cases clay soils tend to hold the water for longer but in a form that is unavailable to plants most of the time. Loam and soils that have loam like silt loam, etc. receive the highest rating due to the fact that the Sands receive lower rating because the water leaves the soil very quickly preventing the plants from utilizing it.

As used herein, drainage class—"Drainage class (natural)" refers to the frequency and duration of wet periods under conditions similar to those under which the soil formed. Alterations of the water regime by human activities, either through drainage or irrigation, are not a consideration unless they have significantly changed the morphology of the soil. In an embodiment, seven classes of natural soil drainage are recognized-excessively drained, somewhat excessively drained, well drained, moderately well drained, somewhat poorly drained, poorly drained, and very poorly drained, as shown in FIG. 16. These classes are defined in the "Soil Survey Manual." In an embodiment, the drainage classes are derived from Schoeneberger, P. J., Wysocki, D. A., Benham, E. C., and Broderson, W. D. (editors), 2002. *Field book for describing and sampling soils*, Version 2.0. Natural Resources Conservation Service, National Soil Survey Center, Lincoln, Nebr., which is hereby incorporated herein by reference.

In an embodiment, the ratings of the soil characteristics are used in a PSPI calculation. For example, the OM, AWC, AWS, Ksat, Surface texture, and Drainage Class ratings may be added together. This creates the initial index for the potential soil productivity index based solely on soil information, e.g., SSURGO, data. In some embodiments, the final output is modified using the topographic wetness index, depending on the precipitation scenarios (normal vs. wet. vs. dry year).

In some embodiments, there are multiple scenarios regarding precipitation. For example, there may be three scenarios: (1) a normal year, (2) a dry year, and (3) a wet year. It should be understood that additional scenarios may be included, for example, an El Nino or La Nina year. For each scenario, the TWI is classified into one or more classes. In the example disclosed here, the TWI is classified into 17 classes, although fewer or more classes may be defined for the TWI. In this example, once the TWI is classified into 17 classes, the classes will be coded in the following manner.

Scenario 1 (normal year)—Rating increases from 1 to 9 for classes 1-9 (increasing TWI), then decreases from 9-1 for classes 10-17 (increasing TWI values). This rating will be used for normal years.

Scenario 2 (dry years)—Rating increases from 1-17 for classes 1-17 with the increase in TWI values. This rating will be used for dry years.

Scenario 3 (wet years)—Rating decreases from 1-17 for classes 1-17 with the increase in TWI values. This rating will be used for wet years.

Once the TWI is classified into classes, raster maps of the PSPI can be produced, as shown in FIG. 2. FIG. 2A provides the PSPI map in a normal year. FIG. 2B provides the PSPI map in a wet year. FIG. 2C provides the PSPI map in a dry year. The maps of PSPI provide one example of a functional soil map based on soil characteristics and elevation models (e.g., TWI is derived from an elevation model). The PSPI map is more spatially explicit compared to the SSURGO map represented by the delineation marker in black in FIGS. 2A, 2B, and 2C. In some embodiments, the accuracy of these maps can be improved by using the continuous soil property maps generated from using fuzzy logic, soil information, and elevation models.

Thus, as disclosed herein, there are multiple methods of determining a relationship between the soil information and the terrain attributes for the area of interest. The system may determine landform classifications and identify soil functional classes based on the soil type, landform class, and terrain attributes for the area of interest. The system may determine fuzzy membership in cells based on soil types, ideal conditions for soil types, and the extracted terrain attributes for every cell in the area of interest. The system may identify the centroid of a soil type polygon and interpolate between the centroids in order to determine a relationship between the soil type and the terrain attributes. In still further embodiments, the system may determine a potential soil productivity index based on one or more characteristics determined for the area of interest. Any method of determining the relationship between the soil information and the terrain attributes may be used in order to develop functional soil maps, as disclosed herein.

In block 112, in some embodiments the system generates fuzzy membership class maps based on the landform classifications. In an embodiment, a fuzzy membership class map is a map created from the fuzzy membership of raster cells created in block 110. For example, ArcSIE assumes a normal distribution of the terrain attributes values for each landform class or soil. This is problematic as it may over or under predict the memberships of each landform class or soil at each pixel. To overcome this limitation, the system fits a piece wise function to the distribution of each terrain attribute within each class using statistical software, e.g., Matlab Software. First a histogram of each terrain attribute within each class is created then fit to a piece wise linear function to the center of the histogram bins, generating a piece wise linear (PWL) membership function. This allows for the next step which is the fitting of different types of distributions to the terrain attributes (Weibul, Lognormal, exponential, etc.), along with the PWL, followed by a test for goodness of fit to determine which fitted curve should be used as the membership function. Then, the membership functions for all terrain attributes and all classes are used to develop fuzzy membership maps for each class using the statistical software. The next step is the use of a series of if-then statements to determine which terrain attributes should be used to define each functional class. For example, if TWI of class 1 is not significantly different from the TWI of other classes, then TWI will not be used to define functional class 1.

In block 114, in some embodiments the system hardens the fuzzy membership soil class maps to produce functional soil classes. In an embodiment, hardening the fuzzy membership maps means combining the fuzzy membership maps created based on soil types and percentage membership in each cell in the map. For example, a raster map of fuzzy membership in soil type A and a raster map of fuzzy membership in soil type B, wherein each cell in both maps has a value of between 0% and 100% membership for the respective soil type, may be combined to create a functional soil class map. In an embodiment, the result is a map having crisp boundaries. In some embodiments, the map is a raster map but in other embodiments the map is a polygon map. In some embodiments, the hardening is performed in ArcSIE.

In block 116, in some embodiments the system generates continuous soil property maps based on the functional soil classes. In this step, the hardened fuzzy membership soil class maps are combined with the soil property values assigned to each soil class. In some embodiments, the selection of soil properties to be assigned to each soil class requires data mining and statistical processing in order to find the representative values for each property and calculate the confidence limits of the predicted maps. Due to the fact that some government soil data (e.g., SSURGO) has been created over an extended period of time based on evolving methods using different tools and scales there are multiple sources of data for soil properties (estimated and measured ones) that often do not agree with each other. For example, FIG. 17 provides representative soil depth values for different functional classes based on different sources of data (soil survey, OSD, and SSURGO representative value). In some embodiments, the system performs a critical evaluation of the data sources for soil properties allowing for the selection of the most accurate data source(s).

As discussed, in some embodiments the soil information is received from polygon soil data. This polygon soil data includes soil properties that are estimates coming from field documentation and/or are measured laboratory data. In some embodiments, the system uses the estimated soil data in combination with the measured soil property data to improve the accuracy of soil property maps. First, the system determines the most representative pixel for each soil class (Pixel which has the highest membership in the prescribed class and lowest membership in all other classes). A code has been developed in Matlab Software to accomplish the task which also takes into account ties. Then the system develops a sampling scheme that selects the most representative location for each soil class. This method minimizes the cost of sampling, while capturing maximum soil variability. The continuous soil property maps are created using a formula that respects the fuzzy soil membership composition of each pixel. Thus, if there are two soils with a certain membership in that pixel the soil property value of that pixel is weighted based on the respective membership of each soil. The resulting product is a continuous soil property map that can be used for site specific crop management and many applications such as precision agriculture, soil nutrient modeling, hydrologic modeling, and regional planning.

Once the raster cells are assigned soil types, the soil characteristics of the soil types may be used to classify the soils. For example, soil A may have a first water holding capacity and soil B may have a second water holding capacity. A cell that is 100% soil A would have the water holding capacity of soil A. A cell that is 50% soil A and 50% soil B would have the average of soil A and soil B's water holding capacity. In this manner, a weighted determination of the characteristic of the soil in the cell is made based on the proportion of the cell that is assigned to different soil types.

In some embodiments, additional sources of data are used to improve the accuracy of the functional soil maps. For example, remotely sensed data may be used to capture soil temperature or landcover. Precipitation records may also be used to create real-time updates the functional soil maps. For example, the functional soil map may be used to assist a farmer in managing irrigation in a field. Additional of current precipitation levels along with soil characteristics may affect the irrigation management strategy. In some embodiments, temperature, light availability, and/or pests are also evaluated and incorporated into the functional soil maps. It should be understood that additional data may improve the functional soil maps to assist users in managing the area of interest for a wide variety of uses.

The functional soil maps or continuous soil property maps may be used by users in management of the area of interest. For example, the maps may be input into an irrigation system to assist in automatic watering of fields according to soil properties. In another example, the map may be input into a pesticide application device to assist in administering pesticides to different areas of a field that differ in their response to pesticide application based on soil and terrain attribute characteristics. Furthermore, the maps may be used to assist in deciding which crops to plant, whether buffers need to be expanded or used, and other management decisions that are impacted by soil functional characteristics.

Turning now to FIG. 3, a block diagram illustrates an environment 300 for determining functional soil maps is provided in accordance with one embodiment of this disclosure. The environment 300 includes a mapping device 144, a management system 142, third party systems 292, external databases 294, and external devices 296. The user 140 is associated with the mapping device 144 and can include an owner of the device 144, parties that have authorized access to the device 144, an employee, associate, and the like. The mapping device 144 can include any type of device such as a desktop computer, a handheld computing device, a server access device, and so forth. The systems and devices communicate with one another over the network 350 and perform one or more of the various steps and/or methods according to embodiments of the disclosure discussed herein.

The network 350 may include a local area network (LAN), a wide area network (WAN), and/or a global area network (GAN). The network 350 may provide for wireline, wireless, or a combination of wireline and wireless communication between devices in the network. In one embodiment, the network 350 includes the Internet.

The mapping device 144 and, in some embodiments, the management system 142 each include a computer system, server, multiple computer systems and/or servers or the like. The mapping device 144, in the embodiments shown has a communication device 212 communicably coupled with a processing device 214, which is also communicably coupled with a memory device 216. The processing device 214 is configured to control the communication device 212 such that the mapping device 144 communicates across the network 350 with one or more other systems. The processing device 214 is also configured to access the memory device 216 in order to read the computer readable instructions 218, which in some embodiments includes soil information applications and terrain attribute applications. The soil information application may be configured to receive soil information and associate it with the terrain attributes. The terrain attribute application may determine terrain attributes from elevation models. The memory device 216 also includes a datastore 222 or database for storing pieces of data that can be accessed by the processing device 214, such as characteristics associated with specific soil types or the like.

As used herein, a "processing device," generally refers to a device or combination of devices having circuitry used for implementing the communication and/or logic functions of a particular system. For example, a processing device may include a digital signal processor device, a microprocessor device, and various analog-to-digital converters, digital-to-analog converters, and other support circuits and/or combinations of the foregoing. Control and signal processing functions of the system are allocated between these processing devices according to their respective capabilities. The processing device 214 and 244 may further include functionality to operate one or more software programs based on computer-executable program code thereof, which may be stored in a memory. As the phrase is used herein, a processing device 214 and 244 may be "configured to" perform a certain function in a variety of ways, including, for example, by having one or more general-purpose circuits perform the function by executing particular computer-executable program code embodied in computer-readable medium, and/or by having one or more application-specific circuits perform the function.

As used herein, a "memory device" generally refers to a device or combination of devices that store one or more forms of computer-readable media and/or computer-executable program code/instructions. Computer-readable media is defined in greater detail below. For example, in one embodiment, the memory device 216 includes any computer memory that provides an actual or virtual space to temporarily or permanently store data and/or commands provided to the processing device 214 when it carries out its functions described herein.

The management system 142 includes a communication device 242 communicably coupled with a processing device 244, which is also communicably coupled with a memory device 246. The processing device 244 is configured to control the communication device 242 such that the management system 142 communicates across the network 350 with one or more other systems. The processing device 244 is also configured to access the memory device 246 in order to read the computer readable instructions 248, which in some embodiments includes an application for implementing a management strategy guided by the functional soil map generated by the mapping device 144. The memory device 246 also includes a datastore 254 or database for storing pieces of data that can be accessed by the processing device 244.

The applications are for instructing the processing devices 214 and 244 to perform various steps of the methods discussed herein, and/or other steps and/or similar steps. In various embodiments, one or more of the applications are included in the computer readable instructions stored in a memory device of one or more systems or devices other than the systems 144 and 142. For example, in some embodiments, the application is stored and configured for being accessed by a processing device of one or more third party systems 292 connected to the network 350. In various embodiments, the applications are stored and executed by different systems/devices. In some embodiments, the applications stored and executed by different systems may be similar and may be configured to communicate with one another, and in some embodiments, the applications may be considered to be working together as a singular application despite being stored and executed on different systems.

FIG. 4 provides a high-level flow chart of a terrain attribute soil mapping process 400, in accordance with an embodiment of this disclosure. In some embodiments, the process includes mining data from digital and analog sources to establish soil-landscape relationships (block 410), quantifying the relationship between soils and their environment (block 412), formalizing the relationships between soils and terrain attributes of the environment (block 414), and creating raster based maps and predicted soil property maps based on the relationships between the soils and the terrain attributes (block 416).

In an embodiment, mining data from digital and analog sources (block 410) includes evaluating county soil survey data, identifying the official soil descriptions (OSD), utilizing SSURGO/soil data mart data, or receiving information from other pre-determined resources. In some embodiments, soils are characterized in a laboratory. In still further embodiments, aerial photography or other types of remote sensing are used to mine data relating to soil-landscape relationships. In some embodiments, tacit knowledge and/or field data and observations is used to supplement or change information received from data sources.

In some embodiments, quantifying the relationship between the soils and their environment (block 412) includes determining terrain attributes for the environment based on at least an elevation model. In some embodiments, the relationships are determined based on block diagrams, soil map unit descriptions, soil data views, and elevation model-derived terrain attributes. For example, TWI, slope, curvature, multi-resolution valley bottom flattens, and ridgetop flattens may be determined. The data may be further analyzed using the soil knowledge miner and based on histograms of frequency of occurrence.

Formalizing the relationship between the soils and their environment may include developing rules for terrain-soil relationships for each relevant terrain attribute. A terrain attribute may be relevant if different soil types differ based on terrain attributes and if terrain attributes control, at least to some degree, the spatial distribution of the soil types on the landscape. For example, if-then statements may be used associated with soil types and terrain attributes.

Finally, in some embodiments, the system creates raster based maps and predicted soil maps (block 416) by assigning a property value to each soil. For example, depth to limiting layer, available water holding capacity, or other properties may be assigned to different soil types for use in assisting management based on soil type. The predicted soil property maps may be based on fuzzy membership values, which predict the soil property at a specific location based on the terrain attributes of the location and the relationships between terrain attributes and soil types.

FIGS. 5, 6, and 7 provide exemplary maps generated via conventional methods and by the Terrain Attribute Soil Mapping process, in accordance with embodiments of this disclosure. FIG. 5 provides a polygon map 500 of soil types generated using SSURGO soil map data. As discussed, the map 500 does not provide information that may be useful to management strategies but instead characterizes the soils based on nomenclature. Also, the displayed polygons (e.g., 502, 504) do not account for terrain attributes that may influence soil properties and/or transitions between soil types. Instead, one soil type changes to a different soil type at a polygon boundary and does not permit gradients of soil functionality. Still further, underlying data issues may cause problems when generating soil maps based on SSURGO data. For example, county boundaries (the vertical boundary 506 centrally located in the map 500) may cause soil types to be inconsistent, as is the case in FIG. 5.

In contrast, FIG. 6 provides a soil map 600 generated via the Terrain Attribute Soil Mapping process. Importantly, the soil map addresses the county boundary issue because the soil classification is based on soil-terrain attribute relationships. The terrain attributes are generated based on a continuous model and are not affected by political boundaries such as county boundaries. In this manner, soil classification is consistent across political boundaries.

In FIG. 7A, a soil depth map 700 based on SSURGO showing the county line boundary 702 is provided and in FIG. 7 B, a continuous soil property map 710 based on TASM using the soil data from the published soil survey manuals is provided. In some embodiments, using different sources of soil data introduces the question of which soil property data source is more accurate. This question was tested by conducting a quick field check (Field Observations marked with green dots). The measured soil depth values were compared with the soil depth maps from SSURGO, OSDs and Published Soil Survey manuals (TASM), and the results are provided in FIG. 8. In this study, the published soil survey manual provided the most accurate soil depth map with an average difference of 25 cm between measured and predicted soil depth for a depth that ranged between 20-200 cm. This provides further evidence that the Terrain Attribute Soil Mapping process results in more accurate categorization and functional information relating to soils than relying on SSURGO or other data types that do not determine a relationship between the soil and terrain attributes in order to generate functional soil maps.

The embodiments of the disclosure may be embodied as a system, method, or computer program product. Accordingly, aspects of the present disclosure may take the form of an entirely hardware embodiment, an entirely software embodiment (including firmware, resident software, microcode, etc.) or an embodiment combining software and hardware aspects that may all generally be referred to herein as a "circuit," "module" or "system." Furthermore, aspects of the present embodiments of the disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing. Computer program code for carrying out operations for aspects of the present embodiments of the disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present embodiments of the disclosure are described herein with reference to flowchart illustrations and/or block diagrams of methods, apparatus (systems) and computer program products according to embodiments of the embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Specific embodiments are described herein. Many modifications and other embodiments of the disclosure set forth herein will come to mind to one skilled in the art to which the disclosure pertains having the benefit of the teachings presented in the foregoing descriptions and the associated drawings. Therefore, it is to be understood that the disclosure is not to be limited to the specific embodiments disclosed and that modifications and other embodiments and combinations of embodiments are intended to be included within the scope of the appended claims. Although specific terms are employed herein, they are used in a generic and descriptive sense only and not for purposes of limitation.

What is claimed is:

1. A system for generating functional soil maps, the system comprising:
   a computer apparatus including a processor and a memory; and
   a software module stored in the memory, comprising executable instructions that when executed by the processor cause the processor to:
   receive electronic data representing soil information for an area of interest;
   determine an elevation model for the area of interest based on elevation data received by the processor, the elevation data corresponding to the area of interest;
   determine terrain attributes for the area of interest based on the elevation model;
   determine a relationship between the soil information and the terrain attributes for the area of interest;
   automatically generate a functional soil map based at least in part on the relationship between the soil information and the terrain attributes for the area of interest; and
   output the functional soil map to an electronic display for a user;
   wherein the soil information comprises a map including one or more polygons corresponding to different soil types;
   wherein each polygon includes an indicator of a primary soil type and one or more secondary soil types;
   wherein the system determines geometric center point locations for the polygons and determine a soil type based on soil property information; and
   wherein continuous soil property predictions are determined by the processor by interpolating the soil property information for the center point locations, the interpolated soil property information displayed within the functional soil map on the electronic display.

2. The system of claim 1, wherein the soil information comprises spatial representations of different soil types in the area of interest.

3. The system of claim 1, wherein the area of interest comprises a geographic area having divergent topography.

4. The system of claim 1, wherein different landforms are aggregated based on the terrain attributes based on similar soil function.

5. A computer-implemented method for generating functional soil maps, the method comprising:
   receiving, via a computing device processor, electronic data representing soil information for an area of interest;
   determining, via the computing device processor, an elevation model for the area of interest based on elevation data received by the processor, the elevation data corresponding to the area of interest;

determining, via the computing device processor, terrain attributes for the area of interest based on the elevation model;

determining, via the computing device processor, a relationship between the soil information and the terrain attributes for the area of interest; and automatically generating, via the computing device processor, a functional soil map based at least in part on the relationship between the soil information and the terrain attributes for the area of interest; and outputting the functional soil map to an electronic display for a user;

wherein the soil information comprises a map including one or more polygons corresponding to different soil types;

wherein each polygon includes an indicator of a primary soil type and one or more secondary soil types;

wherein the method further comprises determining geometric center point locations for the polygons and determine a soil type based on soil property information; and wherein continuous soil property predictions are determined by the processor by interpolating the soil property information for the center point locations, the interpolated soil property information displayed within the functional soil map on the electronic display.

6. The method of claim 5, wherein the soil information comprises spatial representations of different soil types in the area of interest.

7. The method of claim 5, wherein the area of interest comprises a geographic area having divergent topography.

8. The method of claim 5, wherein different landforms are aggregated based on the terrain attributes based on similar soil function.

* * * * *